(12) United States Patent
Dahlmann et al.

(10) Patent No.: US 8,034,748 B2
(45) Date of Patent: *Oct. 11, 2011

(54) ADDITIVES FOR INHIBITING THE FORMATION OF GAS HYDRATES

(75) Inventors: Uwe Dahlmann, Heidelberg (DE); Michael Feustel, Koengernheim (DE)

(73) Assignee: Clariant Produkte (Deutschland) GmbH, Frankfurt (DE)

( * ) Notice: Subject to any disclaimer, the term of this patent is extended or adjusted under 35 U.S.C. 154(b) by 1118 days.

This patent is subject to a terminal disclaimer.

(21) Appl. No.: 11/698,561

(22) Filed: Jan. 26, 2007

(65) Prior Publication Data

US 2007/0129256 A1  Jun. 7, 2007

Related U.S. Application Data

(63) Continuation of application No. 10/483,785, filed on Jan. 13, 2004, now Pat. No. 7,183,240.

(30) Foreign Application Priority Data

Jul. 13, 2001  (DE) .................................. 101 34 224

(51) Int. Cl.
C09K 8/035 (2006.01)
C09K 15/20 (2006.01)
C07C 229/12 (2006.01)
C23F 11/14 (2006.01)

(52) U.S. Cl. ......... 507/90; 507/129; 507/131; 507/133; 507/240; 507/241; 507/244; 507/246; 507/260; 507/261; 507/267; 514/785; 585/15; 560/170; 422/7

(58) Field of Classification Search .......................... None
See application file for complete search history.

(56) References Cited

U.S. PATENT DOCUMENTS

| 4,075,183 | A |   | 2/1978 | Kawakami |
| 4,310,472 | A |   | 1/1982 | Buriks |
| 4,617,132 | A |   | 10/1986 | Dalrymple |
| 4,776,965 | A |   | 10/1988 | Nuesslein |
| 4,959,432 | A |   | 9/1990 | Fan |
| 5,407,775 | A |   | 4/1995 | Larson |
| 5,460,728 | A |   | 10/1995 | Klomp |
| 5,523,433 | A |   | 6/1996 | Toney |
| 5,648,575 | A |   | 7/1997 | Klomp |
| 5,670,476 | A |   | 9/1997 | Vogel |
| 5,879,561 | A |   | 3/1999 | Klomp |
| 5,981,816 | A |   | 11/1999 | Sinquin |
| 6,008,158 | A | * | 12/1999 | Hasebe et al. ................ 504/358 |
| 6,025,302 | A |   | 2/2000 | Pakulski |
| 6,037,315 | A |   | 3/2000 | Franklin |
| 6,152,993 | A |   | 11/2000 | Klomp |
| 6,281,172 | B1 |   | 8/2001 | Warren |
| 6,369,004 | B1 |   | 4/2002 | Klug |
| 6,379,294 | B1 |   | 4/2002 | Buijs |
| 6,444,852 | B1 |   | 9/2002 | Milburn |
| 7,033,504 | B1 |   | 4/2006 | Blytas |
| 7,160,507 | B2 | * | 1/2007 | Dahlmann et al. ................ 422/7 |
| 2004/0159041 | A1 |   | 8/2004 | Dahlmann |
| 2004/0163306 | A1 |   | 8/2004 | Dahlmann |
| 2004/0163307 | A1 |   | 8/2004 | Dahlmann |
| 2004/0164278 | A1 |   | 8/2004 | Dahlmann |
| 2004/0167040 | A1 |   | 8/2004 | Dahlmann |
| 2005/0101495 | A1 |   | 5/2005 | Dahlmann |

FOREIGN PATENT DOCUMENTS

| EP |   | 1043011 A1 | * | 10/2000 |
| WO |   | WO 9413772 |   | 6/1994 |
| WO |   | WO 9414935 |   | 7/1994 |
| WO |   | WO 9845394 A2 | * | 10/1998 |

OTHER PUBLICATIONS

Derwent Abstract of European Patent Appication No. EP 1043011 A1; Dubowoj et al.; Hair Conditioning and Style Treatment; Oct. 11, 2000.*
English Language Abstract of WO 9413772, Dated Jun. 24, 1994.
English Language Abstract of WO 9414935, Dated Jul. 7, 1994.

* cited by examiner

*Primary Examiner* — John J Figueroa
(74) *Attorney, Agent, or Firm* — Tod A. Waldrop

(57) ABSTRACT

The present invention relates to an additive, and its use for inhibiting nucleation, growth and agglomeration of gas hydrates by adding an effective amount of an inhibitor to a multiphasic mixture which tends to hydrate formation and consists of water, gas and optionally condensate, or to a drilling fluid which tends to form gas hydrates. Said inhibitor comprising dialkoxylated quaternary ammonium compounds of the formula 1

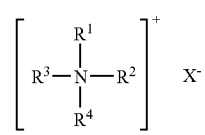

(1)

where $R^1$, $R^2$ are each independently radicals of the formulae $-(A-O)_n-(C)-CO-O-R^5$, $R^3$ is $C_1$- to $C_{30}$-alkyl or $C_2$- to $C_{30}$-alkenyl, $R^4$ is an organic radical which optionally contains heteroatoms and has from 1 to 100 carbon atoms, $R^5$ is an alkyl or an alkenyl, n is a number from 1 to 20, A is an alkylene group, B is an alkylene group, C is a $C_1$- to $C_6$-alkylene group and X is an anion, are used as gas hydrate inhibitors.

8 Claims, No Drawings

ADDITIVES FOR INHIBITING THE FORMATION OF GAS HYDRATES

CROSS-REFERENCE TO RELATED APPLICATIONS

This application is a continuation of U.S. application Ser. No. 10/483,785, filed Jan. 13, 2004, now U.S. Pat. No. 7,183,240 which is hereby incorporated by reference.

The present invention relates to an additive, to its use and to a process for inhibiting nucleation, growth and/or agglomeration of gas hydrates by adding an effective amount of an inhibitor to a multiphasic mixture which tends to hydrate formation and consists of water, gas and optionally condensate, or to a drilling fluid which tends to gas hydrate formation, said inhibitor comprising dialkoxylated quaternary ammonium compounds.

Gas hydrates are crystalline inclusion compounds of gas molecules in water which form under certain temperature and pressure conditions (low temperature and high pressure). The water molecules form cage structures around the appropriate gas molecules. The lattice structure formed from the water molecules is thermodynamically unstable and is only stabilized by the incorporation of guest molecules. Depending on pressure and gas composition, these ice like compounds can exist even to above the freezing point of water (up to above 25° C.).

In the crude oil and natural gas industry, great significance attaches in particular to the gas hydrates which form from water and the natural gas constituents methane, ethane, propane, isobutane, n-butane, nitrogen, carbon dioxide and hydrogen sulfide. Especially in modern natural gas extraction, the existence of these gas hydrates constitutes a great problem, especially when wet gas or multiphasic mixtures of water, gas and alkane mixtures are subjected to low temperatures under high pressure. As a consequence of their insolubility and crystalline structure, the formation of gas hydrates leads here to the blockage of a wide variety of extraction equipment such as pipelines, valves or production equipment in which wet gas or multiphasic mixtures are transported over relatively long distances at relatively low temperatures, as occurs especially in colder regions of the earth or on the seabed.

In addition, gas hydrate formation can also lead to problems in the course of the drilling operation to develop new gas or crude oil deposits at the appropriate pressure and temperature conditions by the formation of gas hydrates in the drilling fluids.

In order to prevent such problems, gas hydrate formation in gas pipelines, in the course of transport of multiphasic mixtures or in drilling fluids, can be suppressed by using relatively large amounts (more than 10% by weight, based on the weight of the aqueous phase) of lower alcohols such as methanol, glycol or diethylene glycol. The addition of these additives has the effect that the thermodynamic limit of gas hydrate formation is shifted to lower temperatures and higher pressures (thermodynamic inhibition). However, the addition of these thermodynamic inhibitors causes serious safety problems (flashpoint and toxicity of the alcohols), logistical problems (large storage tanks, recycling of these solvents) and accordingly high costs, especially in offshore extraction.

Attempts are therefore being made today to replace thermodynamic inhibitors by adding additives in amounts of <2% in temperature and pressure ranges in which gas hydrates can form. These additives either delay gas hydrate formation (kinetic inhibitors) or keep the gas hydrate agglomerates small and therefore pumpable, so that they can be transported through the pipeline (agglomerate inhibitors or anti-agglomerates). The inhibitors used either prevent nucleation and/or the growth of the gas hydrate particles, or modify the hydrate growth in such a way that relatively small hydrate particles result.

The gas hydrate inhibitors which have been described in the patent literature, in addition to the known thermodynamic inhibitors, are a multitude of monomeric and also polymeric substance classes which are kinetic inhibitors or agglomerate inhibitors. Of particular significance in this context are polymers having a carbon backbone which contain both cyclic (pyrrolidone or caprolactam radicals) and acyclic amide structures in the side groups.

EP-B-0 736 130 discloses a process for inhibiting gas hydrates which entails feeding a substance of the formula

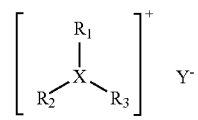

where X=S, N—$R_4$ or P—$R_4$, $R_1$, $R_2$ and $R_3$=alkyl having at least 4 carbon atoms, $R_4$=H or an organic radical, and Y=anion.

This therefore includes compounds of the formula

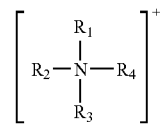

where $R_4$ may be any desired radical, but the $R_1$ to $R_3$ radicals have to be alkyl radicals having at least 4 carbon atoms. No dialkoxylation is disclosed.

EP-B-0 824 631 discloses a process for inhibiting gas hydrates which entails feeding a substance of the formula

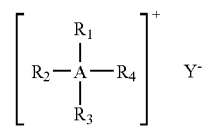

where $R_1$, $R_2$=linear/branched alkyl radicals having 4 or 5 carbon atoms, $R_3$, $R_4$=organic radicals having at least 8 carbon atoms and A=nitrogen or phosphorus. Y⁻ is an anion. Two of the $R_1$ to $R_4$ radicals have to be linear or branched alkyl radicals having 4 or 5 carbon atoms, and no dialkoxylation is disclosed.

U.S. Pat. No. 5,648,575 discloses a process for inhibiting gas hydrates. The process comprises the use of a compound of the formula

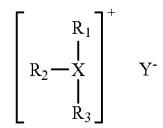

where $R^1$, $R^2$ are linear or branched alkyl groups having at least 4 carbon atoms, $R^3$ is an organic radical having at least 4 atoms, X is sulfur, $NR^4$ or $PR^4$, $R^4$ is hydrogen or an organic radical, and Y is an anion. The document discloses only those compounds which have at least two alkyl radicals having at least 4 carbon atoms, and no dialkoxylation is disclosed.

U.S. Pat. No. 6,025,302 discloses polyetheramine ammonium compounds as gas hydrate inhibitors whose ammonium nitrogen atom, in addition to the polyetheramine chain, bears 3 alkyl substituents.

U.S. Pat. No. 5,523,433 discloses compounds of the formula $$R^a-C(O)-(OCH_2CH_2)_a \diagdown \phantom{x} \diagup R^1$$
$$\phantom{xxxxxxxxxxxxxxxxxxxx} N^+ \phantom{xxx} X^-$$
$$R^b-C(O)-(OCH_2CH_2)_b \diagup \phantom{x} \diagdown R^2$$

where $R^a$ and $R^b$ may each be $C_{12}$- to $C_{22}$-alkyl radicals and $R^1$ and $R^2$ may each be $C_1$- to $C_4$-alkyl radicals. The document discloses the suitability of such compounds as a constituent of fabric softeners.

WO-99/13197 discloses ammonium compounds as gas hydrate inhibitors, which may also be alkoxylated, but not the advantages of di-N-alkoxylation.

WO-01/09082 discloses quaternary amides as gas hydrate inhibitors which, however, bear no alkoxy groups.

WO-00/078 706 discloses quaternary ammonium compounds as gas hydrate inhibitors which, however, bear no carbonyl radicals.

The additives described have only limited effectiveness as kinetic gas hydrate inhibitors and/or antiagglomerates, have to be used with coadditives, or are not obtainable in a sufficient amount or only at high prices.

In order to be able to use gas hydrate inhibitors even at stronger supercooling than currently possible, i.e. further within the hydrate region, a further increase in activity is required in comparison to the prior art hydrate inhibitors. In addition, improved products are desired with regard to their biodegradability, anticorrosive properties and toxicity.

It is thus an object of the present invention to find improved additives which not only slow the formation of gas hydrates (kinetic inhibitors) but also keep gas hydrate agglomerates small and pumpable (antiagglomerates), in order to thus ensure a broad spectrum of application with a high action potential. In addition, it should be possible to replace the thermodynamic inhibitors used currently (methanol and glycols) which cause considerable safety problems and logistical problems.

Prior art gas hydrate inhibitors are commonly coadditized with corrosion inhibitors, in order to prevent corrosion of the transport and extraction equipment. As a consequence of the frequent lack of immediate compatibility of gas hydrate inhibitor and corrosion protector in the course of formulation, there is additional work for the user. It would be a significant advantage over the prior art if coadditization with corrosion inhibitors were no longer obligatory.

It has now been found that, surprisingly, di-N-alkoxylated and carbonylated ammonium salts have excellent action as gas hydrate inhibitors. Their corrosion-inhibiting action is so good that no additization with further corrosion inhibitors is required.

The present invention thus provides the use of compounds of the formula 1

$$\left[ \begin{array}{c} R^1 \\ | \\ R^3-N-R^2 \\ | \\ R^4 \end{array} \right]^+ \phantom{x} X^- \qquad (1)$$

where $R^1$, $R^2$ are each independently radicals of the formulae $$-(B)-(O-A)_n-O-CO-R^5 \qquad (2)$$

or $$-(A-O)_n-(C)-CO-O-R^5 \qquad (3)$$

$R^3$ is $C_1$- to $C_{30}$-alkyl or $C_2$- to $C_{30}$-alkenyl,
$R^4$ is an organic radical which optionally contains heteroatoms and has from 1 to 100 carbon atoms,
$R^5$ is $C_1$- to $C_{30}$-alkyl or $C_2$- to $C_{30}$-alkenyl,
n is a number from 1 to 20,
A is a $C_2$- to $C_4$-alkylene group,
B is a $C_1$- to $C_{10}$-alkylene group,
C is a $C_1$- to $C_6$-alkylene group and
X is an anion
as gas hydrate inhibitors.

The invention further provides a process for inhibiting gas hydrates by adding at least one compound of the formula 1 to a system which tends to form gas hydrates and is composed of water and hydrocarbons.

The invention further provides the compounds of the formula (1), although excluding those compounds in which $R^4$ contains no heteroatom and $R^1$ and $R^2$ are at the same time as defined in formula (2).

In the context of this invention, hydrocarbons are volatile hydrocarbons, for example methane, ethane, propane, butane. For the purposes of this invention, these also include the further gaseous constituents of crude oil/natural gas, for instance hydrogen sulfide and carbon dioxide.

A may be straight-chain or branched and is preferably an ethylene or propylene group, in particular an ethylene group. The alkoxy groups denoted by $(A-O)_n$ may also be mixed alkoxy groups.

B may be straight-chain or branched and is preferably a $C_2$- to $C_4$-alkylene group, in particular an ethylene or propylene group.

C may be straight-chain or branched and is preferably a $C_2$- to $C_4$-alkylene group, in particular a methylene or ethylene group.

n is preferably a number in the range from 2 to 6.

$R^5$ is preferably an alkyl or alkenyl group having from 2 to 24 carbon atoms, in particular from 4 to 12 carbon atoms.

$R^3$ is preferably an alkyl or alkenyl group having from 2 to 12 carbon atoms, in particular those groups having from 4 to 8 carbon atoms and especially butyl groups.

$R^4$ may be any desired organic radical which contains from 1 to 100 carbon atoms and which may contain heteroatoms. When $R^4$ contains hetero-atoms, they are preferably nitrogen or oxygen atoms or both, preferably both. The nitrogen atoms may be present in quaternized form.

In a further preferred embodiment, $R^4$ includes from 1 to 20 alkoxy groups which are derived from $C_2$- to $C_4$-alkylene oxide, in particular from ethylene oxide and/or propylene oxide. In particular, $R^4$ may be a radical of the formula (2) or (3).

In a particularly preferred embodiment, $R^4$ is a radical of the formula (4)

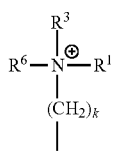
(4)

where the bond to the nitrogen atom in formula 1 is via the free valence of the $(CH_2)_k$ group. In formula (4), $R^6$ is a radical of the formulae $$-(B)-(O-A)_n-O-CO-R^5 \quad (2)$$

or $$-(A-O)_n-(C)-CO-O-R^5 \quad (3)$$

or $C_1$- to $C_{30}$-alkyl or $C_2$- to $C_{30}$-alkenyl, each with the areas of preference specified above for A, B, n, $R^3$ and $R^5$. k is 2 or 3, and $R^1$ and $R^3$ are each as defined above.

Suitable counterions X are all ions which do not impair the solubility of the compounds of the formula (1) in the organic-aqueous mixed phases which tend to gas hydrate formation. Such counterions are, for example, methyl-sulfate ions (methosulfate) or halide ions.

Particularly preferred compounds (illustrated without counterions) correspond to the formulae (5) to (8)

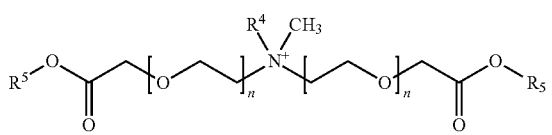
(5)

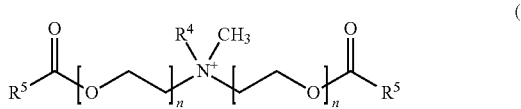
(6)

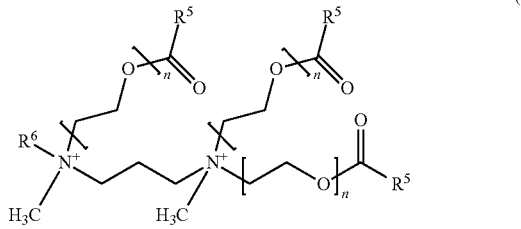
(7)

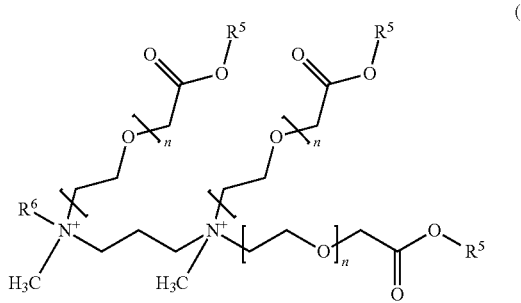
(8)

The inventive compounds can be used alone or in combination with other known gas hydrate inhibitors. In general, enough of the inventive gas hydrate inhibitor will be added to the system which tends to hydrate formation to obtain sufficient inhibition under the given pressure and temperature conditions. The inventive gas hydrate inhibitors are used generally in amounts between 0.01 and 5% by weight (based on the weight of the aqueous phase), corresponding to 100-50 000 ppm, preferably from 0.02 to 1% by weight. When the inventive gas hydrate inhibitors are used in a mixture with other gas hydrate inhibitors, the concentration of the mixture is from 0.01 to 2 or from 0.02 to 1% by weight in the aqueous phase.

For use as gas hydrate inhibitors, the inventive compounds are preferably dissolved in alcoholic solvents such as aqueous monoalcohols, for example methanol, ethanol, propanol, butanol, and also oxyethylated monoalcohols such as butylglycol, isobutylglycol, butyidiglycol and polyglycols. In addition, it has been found that, surprisingly, the inventive compounds of the formula (1) and (4) function as corrosion inhibitors. Additional additization with corrosion inhibitors is therefore in some cases no longer necessary, so that complicated formulation taking into account the compatibility of gas hydrate inhibitor and corrosion protection component for the user is no longer necessary.

The inventive compounds can be prepared by reacting alkoxylated alkylamines or alkylaminoalkylenamines with monochlorocarboxylic acids to give the corresponding ether-carboxylic acids and subsequently esterifying them with alkanols. Alternatively, the bisalkoxylated monoalkyl-amines or alkylaminoalkylenamines can be reacted directly with carboxylic acids and their derivatives such as anhydrides, carbonyl chlorides or their esters to give the inventive esters. This is followed by quatemization with suitable alkylating agents.

The preparation of alkoxylated alkylamines and alkylaminoalkylenamines has been described in the prior art.

The alkoxylated alkylamines used are based on alkylamines having $C_1$- to $C_{30}$-alkyl radicals or $C_2$- to $C_{30}$-alkenyl radicals, preferably $C_3$- to $C_8$-alkylamines. Suitable alkylamines are, for example, n-butylamine, isobutylamine, pentylamine, hexylamine, octylamine, cyclopentylamine, cyclohexylamine.

The alkoxylated alkylaminoalkylenamines used are based on aminoalkylen-amines having $C_1$- to $C_{30}$-alkyl radicals or $C_2$- to $C_{30}$-alkenyl radicals and k=2 or 3. Suitable aminoalkylenamines are, for example, fatty alkyl propylenediamines such as tallow fat propylenediamine, stearylpropylene-diamine, oleylpropylenediamine, laurylpropylenediamine, dodecylpropylenediamine and octylpropylenediamine.

The alkylamines or alkylaminoalkylenamines are generally reacted together with ethylene oxide, propylene oxide, butylene oxide or mixtures of different such alkylene oxides, although preference is given to ethylene oxide or mixtures of ethylene oxide and propylene oxide. Based on alkylamine or alkylaminoalkylenamines, 1-40 mol of alkylene oxide are charged, preferably 1-12 mol.

The alkoxylation is effected without solvent, but can also be carried out in solution. Suitable solvents for the alkoxylation are inert ethers such as dioxane, tetrahydrofuran, glyme, diglyme and MPEGs.

In general, the alkoxylation in the first reaction step is carried out uncatalyzed up to >95% by weight of tertiary nitrogen. Higher alkoxylation is effected after addition of basic compounds as catalysts. Useful basic compounds are alkaline earth metal/alkali metal hydroxides or alkoxides (sodium methoxide, sodium ethoxide, potassium tert-butoxide), but preference is given to alkali metal hydroxides, particularly sodium hydroxide or potassium hydroxide.

For the preparation of the inventive compounds, the amine-oxyethylate mixtures are reacted in a subsequent reaction step with a chlorocarboxylic acid derivative and a base, preferably dry chloroacetic acid sodium salt and sodium hydroxide. This can be effected by reacting the oxyethylate mixture with from 100 to 150 mol % of sodium chloroacetate at from 30 to 100° C. and, simultaneously or in succession, admixing with solid sodium hydroxide or potassium hydroxide, so that the sum of the base already present in the oxyethylate mixture and the additionally added amount of base corresponds to the amount of sodium chloroacetate. The amount of base which has already been contained from the reaction with the alkylene oxide can thus be used directly for the subsequent Williamson synthesis and does not have to be washed out, as in the synthesis of a standard oxyethylate.

Following the alkylation reaction, the alkoxylated amine-ethercarboxylic acid alkali metal salts are converted to the free ethercarboxylic acid. To this end, they are acidified to pH<3 using strong mineral acid (hydrochloric acid, sulfuric acid) and the ethercarboxylic acid is removed hot as the upper phase by phase separation above its cloud point.

The alkoxylated amine-ether carboxylic acids are subsequently esterified generally by direct reaction of the free acid with corresponding alcohols at temperatures of 100-200° C. at which the water of reaction is removed distillatively. The esterification can be accelerated by adding suitable acidic catalysts having a $pK_a$ of less than 5 or by separating out the water of reaction with suitable solvents. Suitable catalysts are, for example, sulfonic acid and alkylstannic acids.

For the esterification of the alkoxylated amine-ether carboxylic acids, alcohols having $C_4$- to $C_{30}$-alkyl radicals or $C_4$- to $C_{30}$-alkenyl radicals are used, preferably fatty alcohols. Suitable alcohols are, for example, 2-ethylhexanol, octanol, decanol, lauryl alcohol, palmityl alcohol, stearyl alcohol and oleyl alcohol.

The inventive compounds can also be prepared by esterifying the amine-oxyethylate mixtures with carboxylic acids and their derivatives such as carbonyl chlorides, carboxylic anhydrides and carboxylic esters. The esterification with free carboxylic acids is effected at temperatures of 100-200° C., at which the water of reaction is removed distillatively. The esterification can be accelerated by adding suitable acidic catalysts having a $pK_a$ of less than 5 or by separating out the water of reaction with suitable solvents. Suitable carboxylic acids are acetic acid, propionic acid, caproic acid, caprylic acid, 2-ethylhexanoic acid and fatty acids, or their anhydrides, methyl esters and chlorides.

The inventive compounds are then prepared by quaternizing the tertiary nitrogen atoms with a suitable alkylating agent at from 50 to 150° C. Suitable alkylating agents are alkyl halides and alkyl sulfates, preferably methylene chloride, butyl bromide and dimethyl sulfate.

EXAMPLES a) General Method for the Preparation of alkoxylated amine-ethercarboxylic Acids A stirred apparatus was initially charged with 2 mol of the appropriate alkoxylated amine or 1 mol of the appropriate alkoxylated diamine (according to OH number) with nitrogen purging and heated to 40° C. 650 g (4.8 mol) of sodium chloroacetate for alkoxylated monoamines or 488 g (3.6 mol) of sodium chloroacetate for alkoxylated diamines were then introduced and the reaction mixture was heated to 50° C. After in each case 30 min, 192 g (4.8 mol) or 144 g (3.6 mol) of NaOH microprills were added in 6 portions in such a way that the temperature did not exceed 55° C. Reaction was continued at 70° C. for 2 h. Afterwards, 10% hydrochloric acid was metered in until a pH of <3 had been attained. The mixture was then heated to 95° C. and transferred to a heatable stirred apparatus having a bottom outlet. The phases were separated after 15 min at 105-108° C. The aqueous lower phase was discarded. In the case of products which cannot be separated by heating above the cloud point, the water of reaction was removed distillatively and the salt which precipitated out was filtered off.

Example 1 cyclopentylamine+2 EO-ECA 370 g of cyclopentylamine+2 EO (OH number: 606.0 mg KOH/g) were used to obtain 600 g of cyclopentylamine+2 EO-ECA having AN=354.2 mg KOH/g (yield 95.0% conversion) and basic N=4.84%.

Example 2 cyclopentylamine+6 EO-ECA 745 g of cyclopentylamine+6 EO (OH number: 301.1 mg KOH/g) were used to obtain 1017 g of cyclopentylamine+6 EO-ECA having AN=212.4 mg KOH/g (corresponding to 92.5% conversion) and basic N=2.84%.

Example 3 cyclohexylamine+2 EO-ECA 398 g of cyclohexylamine+2 EO (OH number: 564.0 mg KOH/g) were used to obtain 627 g of cyclohexylamine+2 EO-ECA having AN=341.6 mg KOH/g (corresponding to 95.9% conversion) and basic N=4.50%.

Example 4 cyclohexylamine+6 EO-ECA 725 g of cyclopentylamine+6 EO (OH number: 309.6 mg KOH/g) were used to obtain 975 g of cyclopentylamine+6 EO-ECA having AN=220.3 mg KOH/g (corresponding to 93.9% conversion) and basic N=2.89%.

Example 5 n-butylamine+2 EO-ECA 346 g of n-butylamine+2 EO (OH number: 648.7 mg KOH/g) were used to obtain 579 g of n-butylamine+2 EO-ECA having AN=377.1 mg KOH/g (corresponding to 97.1% conversion) and basic N=4.62%.

Example 6 n-butylamine+6 EO-ECA 699 g of n-butylamine+6 EO (OH number: 321.1 mg KOH/g) were used to obtain 970 g of n-butylamine+6 EO-ECA having AN=221.5 mg KOH/g (corresponding to 91.9% conversion) and basic N=3.00%.

Example 7 n-butylamine+10 EO-ECA 1032 g of n-butylamine+10 EO (OH number: 217.5 mg KOH/g) were used to obtain 1320 g of n-butylamine+10

EO-ECA having AN=148.7 mg KOH/g (corresponding to 83.7% conversion) and basic N=1.89%.

Example 8 isobutylamine+6 EO-ECA 722 g of isobutylamine+6 EO (OH number: 310.9 mg KOH/g) were used to obtain 995 g of isobutylamine+6 EO-ECA having AN=219.2 mg KOH/g (corresponding to 93.2% conversion) and basic N=3.01%.

Example 9 isobutylamine+10 EO-ECA 1120 g of isobutylamine+10 EO (OH number: 200.4 mg KOH/g) were used to obtain 1384 g of isobutylamine+10 EO-ECA having AN=135.6 mg KOH/g (corresponding to 91.6% conversion) and basic N=2.08%.

Example 10 caprylamine+6 EO-ECA 801 g of caprylamine+6 EO (OH number: 280.1 mg KOH/g) were used to obtain 1045 g of caprylamine+6 EO-ECA having AN=200.9 mg KOH/g (corresponding to 92.5% conversion) and basic N=2.69%.

Example 11 caprylamine+10 EO-ECA 1147 g of caprylamine+10 EO (OH number: 195.7 mg KOH/g) were used to obtain 1412 g of caprylamine+10 EO-ECA having AN=144.9 mg KOH/g (corresponding to 89.0% conversion) and basic N=1.90%.

Example 12 tallow fat propylenediamine+10 EO-ECA 768 g of tallow fat propylenediamine+10 EO (OH number: 219.2 mg KOH/g) were used to obtain 970 g of tallow fat propylenediamine+10 EO-ECA having AN=156.7 mg KOH/g (corresponding to 87.7% conversion) and basic N=2.88%.

Example 13 tallow fat propylenediamine+25 EO-ECA 1316 g of tallow fat propylenediamine+25 EO (OH number: 127.9 mg KOH/g) were used to obtain 1700 g of tallow fat propylenediamine+25 EO-ECA having AN=85.0 mg KOH/g (corresponding to 84.0% conversion) and basic N=1.49%.

Example 14 tallow fat propylenediamine+30 EO-ECA 1699 g of tallow fat propylenediamine+30 EO (OH number: 99.1 mg KOH/g) were used to obtain 2043 g of tallow fat propylenediamine+30 EO-ECA having AN=66.5 mg KOH/g (corresponding to 80.9% conversion) and basic N=1.30%.

Example 15 tallow fat propylenediamine+35 EO-ECA 1919 g of tallow fat propylenediamine+35 EO (OH number: 87.7 mg KOH/g) were used to obtain 2301 g of tallow fat propylenediamine+35 EO-ECA having AN=63.2 mg KOH/g (corresponding to 85.5% conversion) and basic N=1.19%.

Example 16 laurylpropylenediamine+10 EO-ECA 673 g of laurylpropylenediamine+10 EO (OH number: 250.0 mg KOH/g) were used to obtain 1071 g of laurylpropylenediamine+10 EO-ECA having AN=149.2 mg KOH/g (corresponding to 90.5% conversion) and basic N=2.54%.

Example 17 laurylpropylenediamine+30 EO-ECA 1639 g of laurylpropylenediamine+30 EO (OH number: 102.7 mg KOH/g) were used to obtain 1964 g of laurylpropylenediamine+30 EO-ECA having
AN=82.3 mg KOH/g (corresponding to 97.1% conversion) and basic N=1.40%.

General method for the preparation of alkoxylated amine-ethercarboxylic alkyl esters A stirred apparatus was initially charged with 1 mol or 0.5 mol (according to AN) of the appropriate alkoxylated alkylamine- or alkylenediamine-ether-carboxylic acid with nitrogen purging and admixed with an excess (approx. 1.5 molar equivalents) of alcohol. After addition of 0.5% by weight of FASCAT 4100 (butylstannic acid), the mixture was heated to from 100° C. to 180° C. at which the water of reaction distilled off. After a reaction time of 8 hours or attainment of an acid number of AN<5 mg KOH/g, the reaction was ended and excess alcohol and/or residual water were removed distillatively under reduced pressure.

Example 18 cyclopentylamine+2 EO-2-ethylhexyl ECA ester 317 g of cyclopentylamine+2 EO-ECA and 391 g of 2-ethylhexanol were used to obtain 521 g of cyclopentylamine+2 EO-2-ethylhexyl ECA ester having AN=2.8 mg KOH/g and HN=209.3 mg KOH/g (corresponding to 98.7% conversion).

Example 19 cyclopentylamine+6 EO-2-ethylhexyl ECA ester 528 g of cyclopentylamine+6 EO-ECA and 391 g of 2-ethylhexanol were used to obtain 705 g of cyclopentylamine+6 EO-2-ethylhexyl ECA ester having AN=4.9 mg KOH/g and HN=154.1 mg KOH/g (corresponding to 96.8% conversion).

Example 20 cyclohexylamine+2 EO-2-ethylhexyl ECA ester 329 g of cyclohexylamine+2 EO-ECA and 391 g of 2-ethylhexanol were used to obtain 536 g of cyclohexylamine+2

EO-2-ethylhexyl ECA ester having AN=1.8 mg KOH/g and HN=207.2 mg KOH/g (corresponding to 99.1% conversion).

Example 21 cyclohexylamine+6 EO-2-ethylhexyl ECA ester 509 g of cyclopentylamine+6 EO-ECA and 391 g of 2-ethylhexanol were used to obtain 699 g of cyclopentylamine+6 EO-2-ethylhexyl ECA ester having AN=3.3 mg KOH/g and HN=153.4 mg KOH/g (corresponding to 97.8% conversion).

Example 22 n-butylamine+2 EO-2-ethylhexyl ECA ester 298 g of n-butylamine+2 EO-ECA and 391 g of 2-ethylhexanol were used to obtain 503 g of n-butylamine+2 EO-2-ethylhexyl ECA ester having AN=2.4 mg KOH/g and HN=219.5 mg KOH/g (corresponding to 98.9% conversion).

Example 23 n-butylamine+6 EO-2-ethylhexyl ECA ester 507 g of n-butylamine+6 EO-ECA and 391 g of 2-ethylhexanol were used to obtain 707 g of n-butylamine+6 EO-2-ethylhexyl ECA ester having AN=4.1 mg KOH/g and HN=158.1 mg KOH/g (corresponding to 97.4% conversion).

Example 24 n-butylamine+10 EO-dodecyl ECA ester 1032 g of n-butylamine+10 EO-ECA and 559 g of lauryl alcohol were used to obtain 1320 g of n-butylamine+10 EO-dodecyl ECA ester having AN=8.7 mg KOH/g and HN=124.3 mg KOH/g (corresponding to 92.9% conversion).

Example 25 isobutylamine+6 EO-2-ethylhexyl ECA ester 512 g of isobutylamine+6 EO-ECA and 391 g of 2-ethylhexanol were used to obtain 683 g of isobutylamine+6 EO-2-ethylhexyl ECA ester having AN=5.1 mg KOH/g and HN=152.3 mg KOH/g (corresponding to 96.7% conversion).

Example 26 isobutylamine+10 EO-dodecyl ECA ester 1120 g of isobutylamine+10 EO-ECA and 559 g of lauryl alcohol were used to obtain 1384 g of isobutylamine+10 EO-dodecyl ECA ester having AN=5.6 mg KOH/g and HN=115.4 mg KOH/g (corresponding to 95.2% conversion).

Example 27 caprylamine+6 EO-2-ethylhexyl ECA ester 559 g of caprylamine+6 EO-ECA and 391 g of 2-ethylhexanol were used to obtain 738 g of caprylamine+6 EO-2-ethylhexyl ECA ester having AN=3.3 mg KOH/g and HN=147.0 mg KOH/g (corresponding to 97.8% conversion).

Example 28 caprylamine+10 EO-2-ethylhexyl ECA ester 774 g of caprylamine+10 EO-ECA and 391 g of 2-ethylhexanol were used to obtain 999 g of caprylamine+10 EO-2-ethylhexyl ECA ester having AN=4.8 mg KOH/g and HN=114.1 mg KOH/g (corresponding to 95.8% conversion).

Example 29 tallow fat propylenediamine+10 EO-2-ethylhexyl ECA ester 537 g of tallow fat propylenediamine+10 EO-ECA and 293 g of 2-ethylhexanol were used to obtain 688 g of tallow fat propylenediamine+10 EO-2-ethylhexyl ECA ester having AN=4.7 mg KOH/g and HN=121.3 mg KOH/g (corresponding to 96.1% conversion).

Example 30 tallow fat propylenediamine+25 EO-ethylhexyl ECA ester 990 g of tallow fat propylenediamine+25 EO-ECA and 293 g of 2-ethylhexanol were used to obtain 1068 g of tallow fat propylenediamine+25 EO-2-ethylhexyl ECA ester having AN=6.7 mg KOH/g and HN=74.6 mg KOH/g (corresponding to 91.0% conversion).

Example 31 tallow fat propylenediamine+30 EO-ethylhexyl ECA ester 1266 g of tallow fat propylenediamine+30 EO-ECA and 293 g of 2-ethylhexanol were used to obtain 1374 g of tallow fat propylenediamine+30 EO-2-ethylhexyl ECA ester having AN=3.5 mg KOH/g and HN=61.7 mg KOH/g (corresponding to 94.3% conversion).

Example 32 tallow fat propylenediamine+35 EO-dodecyl ECA ester 1332 g of tallow fat propylenediamine+35 EO-ECA and 419 g of lauryl alcohol were used to obtain 1523 g of tallow fat propylenediamine+35 EO-2-dodecyl ECA ester having AN=4.9 mg KOH/g and HN=54.2 mg KOH/g (corresponding to 90.9% conversion).

Example 33 laurylpropylenediamine+10 EO-2-ethylhexyl ECA ester 564 g of laurylpropylenediamine+10 EO-ECA and 293 g of 2-ethylhexanol were used to obtain 703 g of laurylpropylenediamine+10 EO-2-ethylhexyl ECA ester having AN=3.6 mg KOH/g and HN=117.9 mg KOH/g (corresponding to 96.9% conversion).

Example 34 laurylpropylenediamine+30 EO-2-dodecyl ECA ester 1023 g of laurylpropylenediamine+30 EO-ECA and 419 g of lauryl alcohol were used to obtain 1213 g of laurylpropylenediamine+30 EO-2-dodecyl ECA ester having AN=6.0 mg KOH/g and HN=66.8 mg KOH/g (corresponding to 91.0% conversion).

General method for the preparation of alkoxylated aminecarboxylic esters by reacting with carboxylic acids A stirred apparatus was initially charged with 1 mol or 0.5 mol (according to OH number) of the appropriate alkoxylated alkylamine or alkylenediamine with nitrogen purging and admixed with 1 molar equivalent of the appropriate carboxylic acid. After addition of 0.5% by weight of FASCAT 4100 (butylstannic acid), the mixture was heated to from 100° C. to 200° C., at which the water of reaction distilled off. After a reaction time of 8 hours or the attainment of an acid number of AN<10 mg KOH/g, the reaction was ended and the residual water removed distillatively under reduced pressure.

General method for the preparation of alkoxylated aminecarboxylic esters by reacting with carboxylic anhydrides A stirred apparatus was initially charged with 1 mol or 0.5 mol (according to OH number) of the appropriate alkoxylated alkylamine or alkylenediamine with nitrogen purging and admixed with 1 molar equivalent of the appropriate carboxylic anhydride. The mixture was heated to from 100° C. to 150° C. After a reaction time of 8 h at this reaction temperature, the carboxylic acid released was distilled off.

Example 35 n-butylamine+2 EO acetic ester 173 g of n-butylamine+2 EO (OH number: 648.7 mg KOH/g) and 204 g of acetic anhydride were used to obtain 262 g of n-butylamine+2 EO acetic ester having AN=0.4 mg KOH/g and HN=440.7 mg KOH/g.

Example 36 n-butylamine+6 EO acetic ester 349 g of n-butylamine+6 EO (OH number: 321.1 mg KOH/g) and 204 g of acetic anhydride were used to obtain 434 g of n-butylamine+6 EO acetic ester having AN=0.1 mg KOH/g and HN=260.2 mg KOH/g.

Example 37 n-butylamine+6 EO propionic ester 349 g of n-butylamine+6 EO (OH number: 321.1 mg KOH/g) and 260 g of propionic anhydride were used to obtain 465 g of n-butylamine+6 EO propionic ester having AN=0.7 mg KOH/g and HN=244.9 mg KOH/g.

Example 38 n-butylamine+6 EO 2-ethylhexanoic ester 349 g of n-butylamine+6 EO-ECA (OH number: 321.1 mg KOH/g) and 288 g of 2-ethylhexanoic acid were used to obtain 594 g of n-butylamine+6 2-ethylhexanoic ester having AN=6.4 mg KOH/g and HN=191.8 mg KOH/g.

Example 39 caprylamine+6 EO acetic ester 401 g of caprylamine+6 EO (OH number: 280.1 mg KOH/g) and 204 g of acetic anhydride were used to obtain 484 g of caprylamine+6 EO acetic ester having AN=0.2 mg KOH/g and HN=231.5 mg KOH/g.

Example 40 caprylamine+6 EO propionic ester 401 g of caprylamine+6 EO (OH number: 280.1 mg KOH/g) and 260 g of propionic anhydride were used to obtain 517 g of caprylamine+6 EO propionic ester having AN=0.4 mg KOH/g and HN=220.8 mg KOH/g.

Example 41 caprylamine+6 EO 2-ethylhexanoic ester 401 g of caprylamine+6 EO (OH number: 280.1 mg KOH/g) and 288 g of 2-ethylhexanoic acid were used to obtain 643 g of caprylamine+6 EO 2-ethylhexanoic ester having AN=8.1 mg KOH/g and HN=179.6 mg KOH/g.

Example 42 tallow fat propylenediamine+25 EO propionic ester 658 g of tallow fat propylenediamine+25 EO (OH number: 127.9 mg KOH/g) and 195 g of propionic anhydride were used to obtain 750 g of tallow fat propylenediamine+25 EO propionic ester having AN=0.7 mg KOH/g and HN=114.3 mg KOH/g.

Example 43 tallow fat propylenediamine+25 EO 2-ethylhexanoic ester 658 g of tallow fat propylenediamine+25 EO (OH number: 127.9 mg KOH/g) and 216 g of 2-ethylhexanoic acid were used to obtain 859 g of tallow fat propylenediamine+25 EO 2-ethylhexanoic ester having AN=8.6 mg KOH/g and HN=107.6 mg KOH/g.

Example 44 tallow fat propylenediamine+25 EO coconut fatty acid ester 658 g of tallow fat propylenediamine+25 EO (OH number: 127.9 mg KOH/g) and 310 g of coconut fatty acid (AN=271.3 mg KOH/g) were used to obtain 951 g of tallow fat propylenediamine+25 EO coconut fatty acid ester having AN=4.5 mg OH/g and HN=93.9 mg KOH/g.

Example 45 laurylpropylenediamine+30 EO coconut fatty acid ester 820 g of laurylpropylenediamine+30 EO (OH number: 102.7 mg KOH/g) and 310 g of coconut fatty acid (AN=271.3 mg KOH/g) were used to obtain 1107 g of laurylpropylenediamine+30 EO coconut fatty acid ester having AN=3.6 mg KOH/g and HN=79.9 mg KOH/g.

General method for the quaternization of the alkoxylated amine-ethercarboxylic alkyl esters or of the alkoxylated amine-carboxylic esters A stirred apparatus was initially charged with 0.5 mol (according to HN number) of the appropriate alkoxylated amine-ethercarboxylic alkyl ester or of the alkoxylated amine-carboxylic ester with nitrogen purging and heated to 60° C. 0.4 mol of dimethyl sulfate was added dropwise thereto in such a way that the reaction temperature does not exceed 80-90° C. The reaction mixture was subsequently stirred at 90° C. for a further 3 h. This method was used to quaternize the compounds described by Examples 18 to 45 (Examples 46 to 73, as listed in Table 1).

Example 74

Polyvinylcaprolactam having MW 5000 g/mol are mixed in a ratio of 1:1 with the quat described by Example 51 and terminated in butyldiglycol.

Example 75

Polyvinylcaprolactam having MW 5000 g/mol are mixed in a ratio of 1:1 with the quat described by Example 66 and terminated in butyldiglycol.

Effectiveness of the compounds according to the invention as gas hydrate inhibitors To investigate the inhibiting action of the compounds according to the invention, a stirred steel autoclave having temperature control, pressure and torque sensor having an internal volume of 450 ml was used. For investigations of kinetic inhibition, the autoclave was filled with distilled water and gas in a volume ratio of 20:80, and, for investigations of agglomerate inhibition, condensate was additionally added. Finally, natural gas was injected at different pressures.

Starting from a starting temperature of 17.5° C., the autoclave was cooled to 2° C. within 2 h, then stirred at 2° C. for 18 h and heated back up to 17.5° C. within 2 h. An initial pressure decrease corresponding to the thermal compression of the gas is observed. When the formation of gas hydrate nuclei occurs during the supercooling time, the pressure measured falls, and an increase in the torque measured and a slight increase in temperature can be observed. Without inhibitor, further growth and increasing agglomeration of the hydrate nuclei lead rapidly to a further increase in the torque. When the mixture is heated, the gas hydrates decompose, so that the starting state of the experimental series is attained.

The measure used for the inhibiting action of the compounds according to the invention is the time from the attainment of the minimum temperature of 2° C. up to the first gas absorption ($T_{ind}$) or the time up to the rise of the torque ($T_{agg}$). Long induction times or agglomeration times indicate action as a kinetic inhibitor. On the other hand, the torque measured in the autoclave serves as a parameter for the agglomeration of the hydrate crystals. The pressure drop measured ($\Delta p$) allows a direct conclusion on the amount of hydrate crystals formed. In the case of a good anti-agglomerate, the torque which builds up after formation of gas hydrates is distinctly reduced compared to the blank value. Ideally, the snowlike, fine hydrate crystals form in the condensate phase and do not agglomerate and thus do not lead to blockage of the installations serving for gas transport and for gas extraction.

Test Results

Composition of the natural gas used:

Gas 1: 79.3% methane, 10.8% ethane, 4.8% propane, 1.9% butane, 1.4% carbon dioxide, 1.8% nitrogen. Supercooling below the equilibrium temperature of hydrate formation at 50 bar: 12° C.

Gas 2: 92.1% methane, 3.5% ethane, 0.8% propane, 0.7% butane, 0.6% carbon dioxide, 2.3% nitrogen. Supercooling below the equilibrium temperature of hydrate formation at 50 bar: 7° C., supercooling at 100 bar: 12° C.

In order to test the effectiveness as agglomerate inhibitors, the test autoclave used above was initially charged with water and white spirit (20% of the volume in a ratio of 1:2) and, based on the aqueous phase, 5 000 ppm of the particular additive were added. At an autoclave pressure of 90 bar using gas 1 and a stirrer speed of 5 000 rpm, the temperature was cooled from initially 17.5° C. within 2 hours to 2° C., then the mixture was stirred at 2° C. for 25 hours and heated again. The pressure drop caused by hydrate formation and the resulting torque at the stirrer, which is a measure of the agglomeration of the gas hydrates, were measured.

TABLE 1

(Test as antiagglomerant)

| Example | Quat from | Pressure drop $\Delta p$ (bar) | Temperature rise $\Delta T$ (K) | Torque $M_{max}$ (Ncm) |
|---|---|---|---|---|
| Blank value | — | >40 | >8 | 15.9 |
| 46 | Example 18 | 15.1 | 0.3 | 0.3 |
| 47 | Example 19 | 23.1 | 2.2 | 6.3 |
| 48 | Example 20 | 15.3 | 0.7 | 0.4 |
| 49 | Example 21 | 19.9 | 1.9 | 5.7 |
| 50 | Example 22 | 10.1 | 0.1 | 0.2 |
| 51 | Example 23 | 12.3 | 0.2 | 0.2 |
| 52 | Example 24 | 16.8 | 0.8 | 0.9 |
| 53 | Example 25 | 13.4 | 0.2 | 0.3 |
| 54 | Example 26 | 10.9 | 0.2 | 0.3 |
| 55 | Example 27 | 17.4 | 1.9 | 5.8 |
| 56 | Example 28 | 16.6 | 1.0 | 0.9 |
| 57 | Example 29 | 28.5 | 3.2 | 8.8 |
| 58 | Example 30 | 22.1 | 2.5 | 8.3 |
| 59 | Example 31 | 15.8 | 0.8 | 0.5 |
| 60 | Example 32 | 20.6 | 2.0 | 4.9 |
| 61 | Example 33 | 16.2 | 1.1 | 0.9 |
| 62 | Example 34 | 26.8 | 5.1 | 9.2 |
| 63 | Example 35 | 10.3 | 0.1 | 0.1 |
| 64 | Example 36 | 12.8 | 0.4 | 0.5 |
| 65 | Example 37 | 11.6 | 0.4 | 0.4 |
| 66 | Example 38 | 9.4 | 0.0 | 0.0 |
| 67 | Example 39 | 23.0 | 3.5 | 2.4 |
| 68 | Example 40 | 19.0 | 2.5 | 1.4 |
| 69 | Example 41 | 17.0 | 1.5 | 1.2 |
| 70 | Example 42 | 27.1 | 5.9 | 4.8 |
| 71 | Example 43 | 26.8 | 5.8 | 4.4 |
| 72 | Example 44 | 14.8 | 0.8 | 0.9 |
| 73 | Example 45 | 14.5 | 0.5 | 1.0 |
| Comparison | | 21.5 | 1.0 | 1.5 |
| Comparison | | 15.0 | 1.0 | 1.2 |

The comparison substances used were two commercially available antiagglomerant inhibitors based on tetrabutylammonium bromide.

As can be seen from these examples, the torques measured were greatly reduced in comparison to the blank value despite severe hydrate formation. This supports a distinct agglomerate-inhibiting action of the products according to the invention. It is obvious that excellent results are achieved particularly at balanced HL balance.

In order to test the effectiveness as additives for kinetic inhibitors, 5 000 ppm of the particular additive, based on the aqueous phase, were added in the test autoclave described above and cooled at different pressures using gases 1 or 2. On attainment of the minimum temperature of 2° C., the time until the first gas absorption ($T_{ind}$) was recorded. The pressure drop ($\Delta p$) measured and the temperature rise $\Delta T$ (K) allow the amount of hydrate crystals formed to be concluded directly.

TABLE 2

(Test as kinetic inhibitors)

| Example | Inhibitor | Gas | Pressure p (bar) | $T_{ind}$ | Pressure drop $\Delta$ p (bar) | Temperature rise $\Delta$ T (K) |
|---|---|---|---|---|---|---|
| Blank value | — | 1 | 50 | 0 | >40 | >1.5 |
| Blank value | — | 2 | 100 | 0 | >40 | >1.5 |
| 76 | Example 74 | 1 | 50 | 18.5 h | 0 | 0.0 |
| 77 | Example 74 | 2 | 100 | <5 min | 6.8 | 0.2 |
| 78 | Example 75 | 1 | 50 | 9.0 h | 9.7 | 0.4 |
| 79 | Example 75 | 2 | 50 | 6.5 h | 11.2 | 0.3 |
| 80 | Example 75 | 2 | 100 | 1 h | 10.5 | 0.3 |
| Comparison | PVCap | 1 | 50 | <5 min | 10 | 0.4 |
| Comparison | PVCap | 2 | 100 | <5 min | 6 | 0.1 |

The cmparison substance used was a solution of polyvinylcaprolactam (PVCap) in butylglycol, molecular weight 5 000 g/mol.

As can be recognized from the above test results, the products according to the invention act as a synergistic component of kinetic hydrate inhibitors and exhibit a distinct improvement compared to the prior art. They can therefore be used for increasing (synergistic effect) the performance of prior art inhibitors.

The corrosion-inhibiting properties of the compounds according to the invention were demonstrated in the Shell wheel test. Coupons of carbon steel (DIN 1.1203 having 15 cm$^2$ surface area) were immersed in a salt water/petroleum mixture (9:1.5% NaCl solution, adjusted to pH 3.5 using acetic acid) and subjected to this medium at a rotation rate of 40 rpm at 70° C. for 24 hours. The dosage of the inhibitor was 50 ppm of a 40% solution of the inhibitor. The protection values were calculated from the mass reduction of the coupons, based on a blank value.

TABLE 3

(SHELL wheel test)

| Example | Corrosion inhibitor | % protection |
|---|---|---|
| Comparison | | 35-40 |
| 81 | Example 66 | 86-90 |
| 82 | Example 69 | 85-88 |
| 83 | Example 72 | 84-90 |

The products were also tested in the LPR test (test conditions similar to ASTM D2776).

TABLE 4

(LPR test)

| | | Protection after [%] | | |
|---|---|---|---|---|
| Example | Corrosion inhibitor | 10 min | 30 min | 60 min |
| Comparison | | 53.9 | 61.2 | 73.7 |
| 84 | Example 66 | 67.7 | 75.6 | 79.0 |
| 85 | Example 69 | 78.0 | 85.7 | 87.9 |
| 86 | Example 72 | 53.9 | 67.1 | 78.6 |

The comparison substance used in both tests was a residue amine-quat based on dicocoalkyldimethylammonium chloride (prior art corrosion inhibitor).

As can be recognized from the above test results, the inventive gas hydrate inhibitors exhibit corrosion-inhibiting properties and thus constitute a distinct improvement compared to the prior art. When the compounds are used as gas hydrate inhibitors, it is therefore possible in some cases to dispense with additional additization with a corrosion inhibitor. Complicated formulation for the user taking into account the compatibility of gas hydrate inhibitor and corrosion protection component can become unnecessary.

What is claimed is:

1. A process for inhibiting gas hydrates comprising the steps of:
   a) providing a system which forms gas hydrates and is composed of water and hydrocarbons;
   b) providing a compound of the formula 1

(1)

where
R$^1$, R$^2$ are each independently radicals of formula (3)

-(A-O)$_n$—(C)—CO—O—R$^5$ (3)

R$^3$ is C$_1$- to C$_{30}$-alkyl or C$_2$- to C$_{30}$-alkenyl;
R$^4$ is an organic radical which optionally contains heteroatoms and has from 1 to 100 carbon atoms;
R$^5$ is C$_1$- to C$_{30}$-alkyl or C$_2$- to C$_{30}$-alkenyl;
n is a number from 1 to 20;
A is a C$_2$- to C$_4$-alkylene group;
B is a C$_1$- to C$_{10}$-alkylene group;
C is a C$_1$- to C$_6$-alkylene group;
X is an anion; and
adding the compound of formula (1) to a drilling fluid, gas conduit or subterranean formation so that the formation of gas hydrates is inhibited.

2. The process of claim 1, where A is an ethylene or propylene group.

3. The process of claim 1, where B is a C$_2$- to C$_4$-alkylene group.

4. The process of claim 1, where C is a C$_2$- to C$_4$-alkylene group.

5. The process of claim 1, where n is a number in the range from 2 to 6.

6. The process of claim 1, where R$^5$ is an alkyl or alkenyl group having from 2 to 24 carbon atoms.

7. The process of claim 1, where R$^3$ is an alkyl or alkenyl group having from 2 to 12 carbon atoms.

8. The process of claim 1, where $R^4$ is a radical of the formula (4)
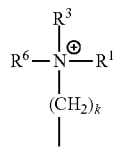
(4)
in which $R^6$ is a radical of the formula (3)
$$-(A\text{-}O)_n\text{—}(C)\text{—}CO\text{—}O\text{—}R^5 \qquad (3)$$
or $C_1$- to $C_{30}$-alkyl or $C_2$- to $C_{30}$-alkenyl and k is 2 or 3.
* * * * *